(12) United States Patent
Jennewine et al.

(10) Patent No.: US 8,641,618 B2
(45) Date of Patent: Feb. 4, 2014

(54) METHOD AND STRUCTURE FOR SECURING A MONITORING DEVICE ELEMENT

(75) Inventors: R. Curtis Jennewine, San Francisco, CA (US); Marc B. Taub, Mountain View, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 1377 days.

(21) Appl. No.: 12/147,462

(22) Filed: Jun. 26, 2008

(65) Prior Publication Data

US 2009/0012377 A1 Jan. 8, 2009

Related U.S. Application Data

(60) Provisional application No. 60/946,492, filed on Jun. 27, 2007.

(51) Int. Cl.
*A61B 5/00* (2006.01)

(52) U.S. Cl.
USPC .......................................................... 600/309

(58) Field of Classification Search
None
See application file for complete search history.

(56) References Cited

U.S. PATENT DOCUMENTS

| | | |
|---|---|---|
| 571,761 A | 11/1896 | Gulliford |
| 1,555,351 A | 9/1925 | Boynton |
| 2,587,707 A | 3/1950 | Dever |
| 2,755,036 A | 7/1956 | Mikko |
| 3,208,121 A | 9/1965 | Price |
| 3,923,060 A | 12/1975 | Ellinwood, Jr. |
| 3,924,819 A | 12/1975 | Lapinskas |
| 4,003,379 A | 1/1977 | Ellinwood, Jr. |
| 4,055,175 A | 10/1977 | Clemens et al. |
| 4,076,182 A | 2/1978 | Stites |
| 4,151,845 A | 5/1979 | Clemens |
| 4,360,019 A | 11/1982 | Portner |
| 4,387,863 A | 6/1983 | Edmonston |
| 4,601,707 A | 7/1986 | Albisser et al. |
| 4,629,145 A | 12/1986 | Graham |
| 4,667,896 A | 5/1987 | Frey et al. |
| 4,685,903 A | 8/1987 | Cable et al. |
| 4,725,010 A | 2/1988 | Lotamer |
| 4,802,638 A | 2/1989 | Burger et al. |
| 4,886,505 A | 12/1989 | Haynes et al. |
| 5,019,096 A | 5/1991 | Fox, Jr. et al. |
| 5,067,665 A | 11/1991 | LoStracco et al. |
| 5,097,834 A | 3/1992 | Skrabal |
| 5,109,577 A | 5/1992 | Young |
| 5,209,414 A | 5/1993 | Clemens et al. |
| 5,236,143 A | 8/1993 | Dragon |
| 5,237,993 A | 8/1993 | Skrabal |
| 5,250,023 A | 10/1993 | Lee |
| 5,251,126 A | 10/1993 | Kahn et al. |
| 5,266,359 A | 11/1993 | Spielvogel |
| 5,344,411 A | 9/1994 | Domb et al. |
| 5,349,852 A | 9/1994 | Kamen et al. |
| 5,390,671 A | 2/1995 | Lord et al. |
| 5,394,877 A | 3/1995 | Orr et al. |
| 5,402,780 A | 4/1995 | Faasse, Jr. |
| 5,437,656 A | 8/1995 | Shikani et al. |
| 5,451,424 A | 9/1995 | Solomon et al. |
| 5,526,844 A | 6/1996 | Kamen et al. |
| 5,533,389 A | 7/1996 | Kamen et al. |
| 5,558,640 A | 9/1996 | Pfeiler |
| 5,569,186 A | 10/1996 | Lord et al. |
| 5,593,852 A | 1/1997 | Heller et al. |
| 5,599,321 A | 2/1997 | Conway et al. |
| 5,601,435 A | 2/1997 | Quy |
| 5,609,575 A | 3/1997 | Larson et al. |
| 5,662,904 A | 9/1997 | Ferguson et al. |
| 5,673,691 A | 10/1997 | Abrams et al. |
| 5,807,375 A | 9/1998 | Gross et al. |
| 5,822,715 A | 10/1998 | Worthington et al. |
| 5,899,855 A | 5/1999 | Brown |
| 5,918,603 A | 7/1999 | Brown |
| 5,925,021 A | 7/1999 | Castellano et al. |
| 5,951,521 A | 9/1999 | Mastrototaro et al. |
| 5,954,643 A | 9/1999 | VanAntwerp et al. |
| 5,956,501 A | 9/1999 | Brown |
| 5,975,120 A | 11/1999 | Novosel |
| 5,987,353 A | 11/1999 | Khatchatrian et al. |
| 5,988,545 A | 11/1999 | King |
| 6,004,278 A | 12/1999 | Botich et al. |
| 6,083,248 A | 7/2000 | Thompson |
| 6,091,975 A * | 7/2000 | Daddona et al. ............. 600/345 |
| 6,129,823 A * | 10/2000 | Hughes et al. ............ 204/403.1 |
| 6,134,461 A | 10/2000 | Say et al. |
| 6,141,573 A | 10/2000 | Kurnik et al. |
| 6,175,752 B1 | 1/2001 | Say et al. |
| 6,233,539 B1 | 5/2001 | Brown |
| 6,247,664 B1 | 6/2001 | Peterson et al. |
| 6,248,067 B1 | 6/2001 | Causey et al. |
| 6,254,586 B1 | 7/2001 | Mann et al. |
| 6,284,478 B1 | 9/2001 | Heller et al. |
| 6,379,301 B1 | 4/2002 | Worthington et al. |
| 6,418,332 B1 | 7/2002 | Mastrototaro et al. |
| 6,427,088 B1 | 7/2002 | Bowman, IV et al. |
| 6,471,689 B1 | 10/2002 | Joseph et al. |

(Continued)

FOREIGN PATENT DOCUMENTS

| | | |
|---|---|---|
| CA | 2291105 | 12/1998 |
| EP | 0987982 | 1/2007 |

(Continued)

OTHER PUBLICATIONS

U.S. Appl. No. 13/118,441, Office Action mailed Apr. 25, 2013.

*Primary Examiner* — Agnieszka Boesen
(74) *Attorney, Agent, or Firm* — Jackson & Co., LLP

(57) ABSTRACT

Structures and methods for attaching a device to a user's skin are provided. Embodiments include refreshing an adhesive attaching an element of an analyte monitoring device so that a first adhesive attaches the element of the analyte monitoring device during a first time period and a second adhesive attaches the element of the analyte monitoring device to the user's skin during a second time period. A sensor remains at least partially inserted into the user's while the refreshing of the adhesive from the first to the second adhesive occurs.

10 Claims, 10 Drawing Sheets

(56) References Cited

U.S. PATENT DOCUMENTS

| | | |
|---|---|---|
| 6,482,156 B2 | 11/2002 | Iliff |
| 6,484,045 B1 | 11/2002 | Holker et al. |
| 6,485,461 B1 | 11/2002 | Mason et al. |
| 6,554,798 B1 | 4/2003 | Mann et al. |
| 6,558,321 B1 | 5/2003 | Burd et al. |
| 6,558,351 B1 | 5/2003 | Steil et al. |
| 6,562,001 B2 | 5/2003 | Lebel et al. |
| 6,564,105 B2 | 5/2003 | Starkweather et al. |
| 6,571,128 B2 | 5/2003 | Lebel et al. |
| 6,576,101 B1 | 6/2003 | Heller et al. |
| 6,577,899 B2 | 6/2003 | Lebel et al. |
| 6,585,644 B2 | 7/2003 | Lebel et al. |
| 6,598,824 B2 | 7/2003 | Schmidt |
| 6,635,014 B2 | 10/2003 | Starkweather et al. |
| 6,641,562 B1 | 11/2003 | Peterson |
| 6,648,821 B2 | 11/2003 | Lebel et al. |
| 6,656,114 B1 | 12/2003 | Poulson et al. |
| 6,656,158 B2 | 12/2003 | Mahoney et al. |
| 6,656,159 B2 | 12/2003 | Flaherty |
| 6,658,396 B1 | 12/2003 | Tang et al. |
| 6,659,948 B2 | 12/2003 | Lebel et al. |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,692,457 B2 | 2/2004 | Flaherty |
| 6,694,191 B2 | 2/2004 | Starkweather et al. |
| 6,699,218 B2 | 3/2004 | Flaherty et al. |
| 6,702,857 B2 | 3/2004 | Brauker et al. |
| 6,723,072 B2 | 4/2004 | Flaherty et al. |
| 6,733,446 B2 | 5/2004 | Lebel et al. |
| 6,736,797 B1 | 5/2004 | Larsen et al. |
| 6,740,059 B2 | 5/2004 | Flaherty |
| 6,740,075 B2 | 5/2004 | Lebel et al. |
| 6,741,877 B1 | 5/2004 | Shults et al. |
| 6,744,350 B2 | 6/2004 | Blomquist |
| 6,749,587 B2 | 6/2004 | Flaherty |
| 6,758,810 B2 | 7/2004 | Lebel et al. |
| 6,768,425 B2 | 7/2004 | Flaherty et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,830,558 B2 | 12/2004 | Flaherty et al. |
| 6,837,858 B2 | 1/2005 | Cunningham et al. |
| 6,852,104 B2 | 2/2005 | Blomquist |
| 6,862,465 B2 | 3/2005 | Shults et al. |
| 6,873,268 B2 | 3/2005 | Lebel et al. |
| 6,882,940 B2 | 4/2005 | Potts et al. |
| 6,887,270 B2 | 5/2005 | Miller et al. |
| 6,896,666 B2 | 5/2005 | Kochamaba et al. |
| 6,902,207 B2 | 6/2005 | Lickliter |
| 6,916,159 B2 | 7/2005 | Rush et al. |
| 6,931,327 B2 | 8/2005 | Goode, Jr. et al. |
| 6,936,006 B2 | 8/2005 | Sabra |
| 6,946,446 B2 | 9/2005 | Ma et al. |
| 6,950,708 B2 | 9/2005 | Bowman, IV et al. |
| 6,958,705 B2 | 10/2005 | Lebel et al. |
| 6,960,192 B1 | 11/2005 | Flaherty et al. |
| 6,974,437 B2 | 12/2005 | Lebel et al. |
| 7,003,336 B2 | 2/2006 | Holker et al. |
| 7,018,360 B2 | 3/2006 | Flaherty et al. |
| 7,024,245 B2 | 4/2006 | Lebel et al. |
| 7,029,455 B2 | 4/2006 | Flaherty |
| 7,034,677 B2 | 4/2006 | Steinthal et al. |
| 7,052,251 B2 | 5/2006 | Nason et al. |
| 7,052,472 B1 | 5/2006 | Miller et al. |
| 7,066,922 B2 | 6/2006 | Angel et al. |
| 7,074,307 B2 | 7/2006 | Simpson et al. |
| 7,077,328 B2 | 7/2006 | Krishnaswamy et al. |
| 7,079,977 B2 | 7/2006 | Osorio et al. |
| 7,081,195 B2 | 7/2006 | Simpson et al. |
| 7,092,891 B2 | 8/2006 | Maus et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,133,717 B2 | 11/2006 | Coston et al. |
| 7,134,999 B2 | 11/2006 | Brauker et al. |
| 7,136,689 B2 | 11/2006 | Shults et al. |
| 7,137,964 B2 | 11/2006 | Flaherty |
| 7,144,384 B2 | 12/2006 | Gorman et al. |
| 7,155,112 B2 | 12/2006 | Uno et al. |
| 7,167,818 B2 | 1/2007 | Brown |
| 7,171,274 B2 | 1/2007 | Starkweather et al. |
| 7,171,312 B2 | 1/2007 | Steinthal et al. |
| 7,192,450 B2 | 3/2007 | Brauker et al. |
| 7,207,974 B2 | 4/2007 | Safabash et al. |
| 7,216,665 B1 | 5/2007 | Sims, Jr. |
| 7,226,278 B2 | 6/2007 | Nason et al. |
| 7,226,978 B2 | 6/2007 | Tapsak et al. |
| 7,229,042 B2 | 6/2007 | Thebault et al. |
| 7,267,665 B2 | 9/2007 | Steil et al. |
| 7,276,029 B2 | 10/2007 | Goode, Jr. et al. |
| 7,303,549 B2 | 12/2007 | Flaherty et al. |
| 7,310,544 B2 | 12/2007 | Brister et al. |
| 7,318,816 B2 | 1/2008 | Bobroff et al. |
| 7,324,012 B2 | 1/2008 | Mann et al. |
| 7,329,239 B2 | 2/2008 | Safabash et al. |
| 7,335,294 B2 | 2/2008 | Heller et al. |
| 7,354,420 B2 | 4/2008 | Steil et al. |
| 7,364,568 B2 | 4/2008 | Angel et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,402,153 B2 | 7/2008 | Steil et al. |
| 7,424,318 B2 | 9/2008 | Brister et al. |
| 7,429,258 B2 | 9/2008 | Angel et al. |
| 7,455,663 B2 | 11/2008 | Bikovsky |
| 7,460,898 B2 | 12/2008 | Brister et al. |
| 7,462,264 B2 | 12/2008 | Heller et al. |
| 7,467,003 B2 | 12/2008 | Brister et al. |
| 7,471,972 B2 | 12/2008 | Rhodes et al. |
| 7,483,736 B2 | 1/2009 | Marchitto et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,519,408 B2 | 4/2009 | Rasdal et al. |
| 7,547,281 B2 | 6/2009 | Hayes et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,645,263 B2 | 1/2010 | Angel et al. |
| 7,651,596 B2 | 1/2010 | Petisce et al. |
| 7,651,845 B2 | 1/2010 | Doyle, III et al. |
| 7,654,956 B2 | 2/2010 | Brister et al. |
| 7,657,297 B2 | 2/2010 | Simpson et al. |
| 7,697,967 B2 | 4/2010 | Stafford |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,147 B1 | 6/2010 | Osorio et al. |
| 7,731,657 B2 | 6/2010 | Stafford |
| 7,736,310 B2 * | 6/2010 | Taub .......................... 600/309 |
| 7,736,344 B2 | 6/2010 | Moberg et al. |
| 7,763,042 B2 | 7/2010 | Iio et al. |
| 7,766,829 B2 | 8/2010 | Sloan et al. |
| 7,822,454 B1 | 10/2010 | Alden et al. |
| 8,010,174 B2 | 8/2011 | Goode et al. |
| 8,085,151 B2 | 12/2011 | Jennewine |
| 8,282,549 B2 | 10/2012 | Brauker et al. |
| 2001/0020124 A1 | 9/2001 | Tamada |
| 2001/0047604 A1 | 12/2001 | Valiulis |
| 2002/0016719 A1 | 2/2002 | Nemeth et al. |
| 2002/0106709 A1 | 8/2002 | Potts et al. |
| 2002/0107476 A1 | 8/2002 | Mann et al. |
| 2002/0133107 A1 | 9/2002 | Darcey |
| 2002/0147135 A1 | 10/2002 | Schnell |
| 2002/0169635 A1 | 11/2002 | Shillingburg |
| 2002/0193679 A1 | 12/2002 | Malave et al. |

(56) References Cited

U.S. PATENT DOCUMENTS

| | | |
|---|---|---|
| 2003/0021729 A1* | 1/2003 | Moller et al. ............... 422/68.1 |
| 2003/0023317 A1 | 1/2003 | Brauker et al. |
| 2003/0028089 A1 | 2/2003 | Galley et al. |
| 2003/0032874 A1 | 2/2003 | Rhodes et al. |
| 2003/0060753 A1 | 3/2003 | Starkweather et al. |
| 2003/0065308 A1 | 4/2003 | Lebel et al. |
| 2003/0069541 A1 | 4/2003 | Gillis et al. |
| 2003/0073414 A1 | 4/2003 | P. Capps |
| 2003/0114836 A1 | 6/2003 | Estes et al. |
| 2003/0122021 A1 | 7/2003 | McConnell et al. |
| 2003/0130616 A1 | 7/2003 | Steil et al. |
| 2003/0144362 A1 | 7/2003 | Utterberg et al. |
| 2003/0175323 A1 | 9/2003 | Utterberg et al. |
| 2003/0176933 A1 | 9/2003 | Lebel et al. |
| 2003/0212379 A1 | 11/2003 | Bylund et al. |
| 2003/0217966 A1 | 11/2003 | Tapsak et al. |
| 2004/0011671 A1 | 1/2004 | Shults et al. |
| 2004/0045879 A1 | 3/2004 | Shults et al. |
| 2004/0122530 A1 | 6/2004 | Hansen et al. |
| 2004/0133390 A1 | 7/2004 | Osorio et al. |
| 2004/0135684 A1 | 7/2004 | Steinthal et al. |
| 2004/0152622 A1 | 8/2004 | Keith et al. |
| 2004/0155770 A1 | 8/2004 | Nelson et al. |
| 2004/0162521 A1 | 8/2004 | Bengtsson |
| 2004/0167464 A1 | 8/2004 | Ireland et al. |
| 2004/0186362 A1 | 9/2004 | Brauker et al. |
| 2004/0193025 A1 | 9/2004 | Steil et al. |
| 2004/0193090 A1 | 9/2004 | Lebel et al. |
| 2004/0199059 A1 | 10/2004 | Brauker et al. |
| 2004/0210180 A1 | 10/2004 | Altman |
| 2004/0210208 A1 | 10/2004 | Paul et al. |
| 2004/0225338 A1 | 11/2004 | Lebel et al. |
| 2004/0254433 A1 | 12/2004 | Bandis et al. |
| 2004/0260478 A1 | 12/2004 | Schwamm |
| 2005/0004439 A1 | 1/2005 | Shin et al. |
| 2005/0010269 A1 | 1/2005 | Lebel et al. |
| 2005/0027180 A1 | 2/2005 | Goode, Jr. et al. |
| 2005/0031689 A1 | 2/2005 | Shults et al. |
| 2005/0038332 A1 | 2/2005 | Saidara et al. |
| 2005/0038674 A1 | 2/2005 | Braig et al. |
| 2005/0043598 A1 | 2/2005 | Goode, Jr. et al. |
| 2005/0049179 A1 | 3/2005 | Davidson et al. |
| 2005/0065464 A1 | 3/2005 | Talbot et al. |
| 2005/0090607 A1 | 4/2005 | Tapsak et al. |
| 2005/0096511 A1 | 5/2005 | Fox et al. |
| 2005/0112169 A1 | 5/2005 | Brauker et al. |
| 2005/0113653 A1 | 5/2005 | Fox et al. |
| 2005/0119540 A1 | 6/2005 | Potts et al. |
| 2005/0137530 A1 | 6/2005 | Campbell et al. |
| 2005/0143635 A1 | 6/2005 | Kamath et al. |
| 2005/0171512 A1 | 8/2005 | Flaherty |
| 2005/0176136 A1 | 8/2005 | Burd et al. |
| 2005/0181010 A1 | 8/2005 | Hunter et al. |
| 2005/0182306 A1 | 8/2005 | Sloan |
| 2005/0182358 A1 | 8/2005 | Veit et al. |
| 2005/0182366 A1 | 8/2005 | Vogt et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0203360 A1 | 9/2005 | Brauker et al. |
| 2005/0203461 A1 | 9/2005 | Flaherty et al. |
| 2005/0238507 A1 | 10/2005 | DiIanni et al. |
| 2005/0245795 A1 | 11/2005 | Goode et al. |
| 2005/0245799 A1 | 11/2005 | Brauker et al. |
| 2005/0261667 A1 | 11/2005 | Crank et al. |
| 2005/0277872 A1 | 12/2005 | Colby et al. |
| 2005/0277912 A1 | 12/2005 | John |
| 2006/0001551 A1 | 1/2006 | Kraft et al. |
| 2006/0004603 A1 | 1/2006 | Peterka et al. |
| 2006/0010098 A1 | 1/2006 | Goodnow et al. |
| 2006/0015020 A1 | 1/2006 | Neale et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0041229 A1 | 2/2006 | Garibotto et al. |
| 2006/0065772 A1 | 3/2006 | Grant et al. |
| 2006/0079740 A1 | 4/2006 | Silver et al. |
| 2006/0095020 A1 | 5/2006 | Casas et al. |
| 2006/0154642 A1 | 7/2006 | Scannell |
| 2006/0166629 A1 | 7/2006 | Reggiardo |
| 2006/0173406 A1 | 8/2006 | Hayes et al. |
| 2006/0173444 A1 | 8/2006 | Choy et al. |
| 2006/0173712 A1 | 8/2006 | Joubert |
| 2006/0178633 A1 | 8/2006 | Garibotto et al. |
| 2006/0189863 A1 | 8/2006 | Peyser et al. |
| 2006/0222566 A1 | 10/2006 | Brauker et al. |
| 2006/0224141 A1 | 10/2006 | Rush et al. |
| 2006/0226985 A1 | 10/2006 | Goodnow et al. |
| 2006/0247508 A1 | 11/2006 | Fennell |
| 2006/0272652 A1 | 12/2006 | Stocker et al. |
| 2006/0282290 A1 | 12/2006 | Flaherty et al. |
| 2006/0293577 A1 | 12/2006 | Morrison et al. |
| 2007/0016381 A1 | 1/2007 | Kamath et al. |
| 2007/0027381 A1 | 2/2007 | Stafford |
| 2007/0060869 A1 | 3/2007 | Tolle et al. |
| 2007/0060870 A1 | 3/2007 | Tolle et al. |
| 2007/0060871 A1 | 3/2007 | Istoc et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078818 A1 | 4/2007 | Zvitz et al. |
| 2007/0093786 A1 | 4/2007 | Goldsmith et al. |
| 2007/0100222 A1 | 5/2007 | Mastrototaro et al. |
| 2007/0106135 A1 | 5/2007 | Sloan et al. |
| 2007/0118405 A1 | 5/2007 | Campbell et al. |
| 2007/0128682 A1 | 6/2007 | Rosman et al. |
| 2007/0129621 A1 | 6/2007 | Kellogg et al. |
| 2007/0149875 A1 | 6/2007 | Ouyang et al. |
| 2007/0163880 A1 | 7/2007 | Woo et al. |
| 2007/0191702 A1 | 8/2007 | Yodfat et al. |
| 2007/0203407 A1 | 8/2007 | Hoss et al. |
| 2007/0203966 A1 | 8/2007 | Brauker et al. |
| 2007/0208246 A1 | 9/2007 | Brauker et al. |
| 2007/0213657 A1 | 9/2007 | Jennewine et al. |
| 2007/0219480 A1 | 9/2007 | Kamen et al. |
| 2007/0219597 A1 | 9/2007 | Kamen et al. |
| 2007/0228071 A1 | 10/2007 | Kamen et al. |
| 2007/0235331 A1 | 10/2007 | Simpson et al. |
| 2007/0249922 A1 | 10/2007 | Peyser et al. |
| 2007/0255114 A1 | 11/2007 | Ackermann et al. |
| 2007/0299409 A1 | 12/2007 | Whitbourne et al. |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0018480 A1 | 1/2008 | Sham |
| 2008/0021666 A1 | 1/2008 | Goode, Jr. et al. |
| 2008/0033254 A1 | 2/2008 | Kamath et al. |
| 2008/0033268 A1 | 2/2008 | Stafford |
| 2008/0039702 A1 | 2/2008 | Hayter et al. |
| 2008/0045824 A1 | 2/2008 | Tapsak et al. |
| 2008/0064937 A1 | 3/2008 | McGarraugh et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0093447 A1 | 4/2008 | Johnson et al. |
| 2008/0097246 A1 | 4/2008 | Stafford |
| 2008/0108942 A1 | 5/2008 | Brister et al. |
| 2008/0119707 A1 | 5/2008 | Stafford |

(56) References Cited

U.S. PATENT DOCUMENTS

| | | |
|---|---|---|
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200897 A1 | 8/2008 | Hoss et al. |
| 2008/0201325 A1 | 8/2008 | Doniger et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0262469 A1 | 10/2008 | Brister et al. |
| 2008/0269687 A1 | 10/2008 | Chong et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0012379 A1 | 1/2009 | Goode, Jr. et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0054745 A1 | 2/2009 | Jennewine et al. |
| 2009/0062633 A1 | 3/2009 | Brauker et al. |
| 2009/0062635 A1 | 3/2009 | Brauker et al. |
| 2009/0069650 A1 | 3/2009 | Jennewine et al. |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0088614 A1 | 4/2009 | Taub |
| 2009/0088787 A1 | 4/2009 | Koike et al. |
| 2009/0099436 A1 | 4/2009 | Brister et al. |
| 2009/0102678 A1 | 4/2009 | Mazza et al. |
| 2009/0105569 A1 | 4/2009 | Stafford |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0113897 A1 | 5/2010 | Brenneman et al. |
| 2010/0119693 A1 | 5/2010 | Tapsak et al. |
| 2010/0121169 A1 | 5/2010 | Petisce et al. |
| 2010/0152554 A1 | 6/2010 | Steine et al. |
| 2010/0174157 A1 | 7/2010 | Brister et al. |
| 2010/0185069 A1 | 7/2010 | Brister et al. |
| 2010/0198142 A1 | 8/2010 | Sloan et al. |
| 2010/0217105 A1 | 8/2010 | Yodfat et al. |
| 2010/0262201 A1 | 10/2010 | He et al. |
| 2010/0292634 A1 | 11/2010 | Kircher et al. |
| 2010/0331642 A1 | 12/2010 | Bruce et al. |
| 2011/0040256 A1 | 2/2011 | Bobroff et al. |
| 2011/0178461 A1 | 7/2011 | Chong et al. |

FOREIGN PATENT DOCUMENTS

| | | |
|---|---|---|
| EP | 2327362 | 6/2011 |
| EP | 2335587 | 6/2011 |
| WO | WO-01/52935 | 7/2001 |
| WO | WO-01/54753 | 8/2001 |
| WO | WO-2006/037109 | 4/2006 |
| WO | WO-2007/101260 | 9/2007 |
| WO | WO-2008/003003 | 1/2008 |
| WO | WO-2008/005780 | 1/2008 |
| WO | WO-2011/002815 | 1/2011 |

* cited by examiner

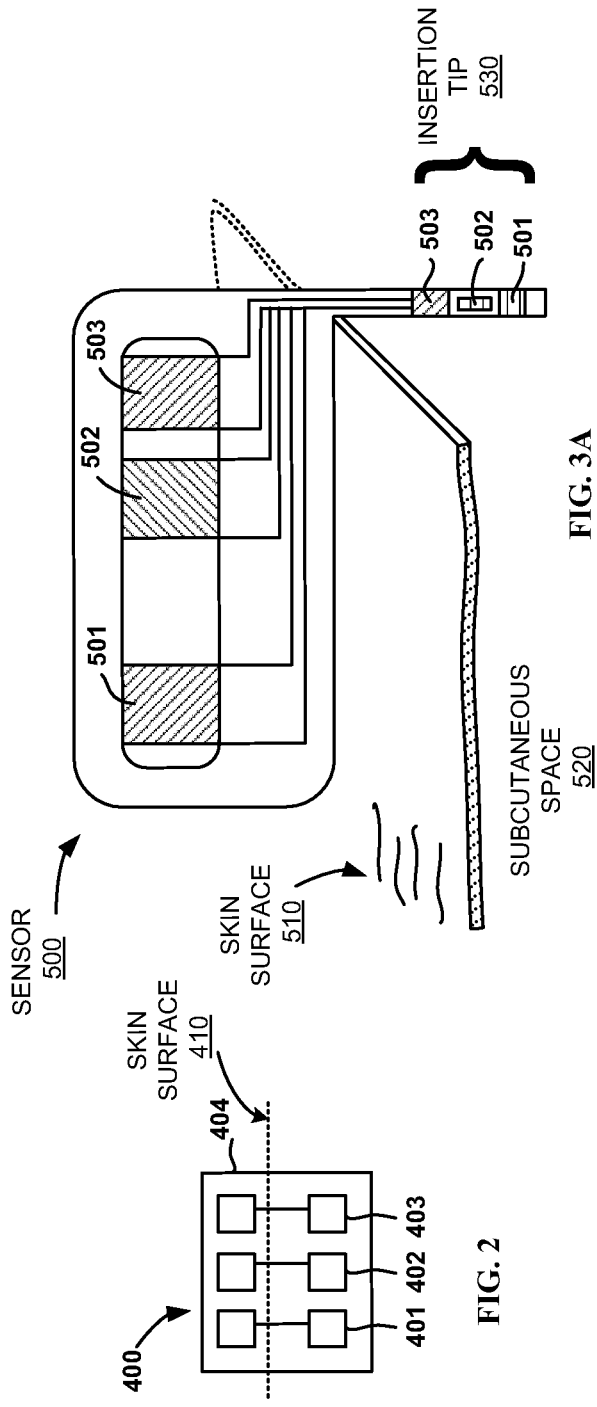
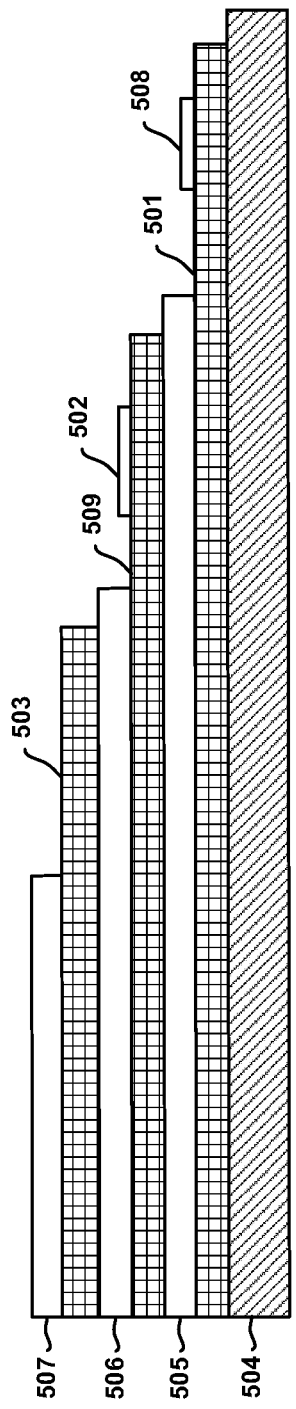

METHOD AND STRUCTURE FOR SECURING A MONITORING DEVICE ELEMENT

RELATED APPLICATION

The present application claims priority under §35 U.S.C. 119(e) to U.S. provisional application No. 60/946,492 filed Jun. 27, 2007 entitled "Method and Structure for Securing a Monitoring Device Element," and assigned to the assignee of the present application, Abbott Diabetes Care Inc. of Alameda, Calif., the disclosure of which is incorporated by reference for all purposes.

BACKGROUND

The detection of the level of analytes, such as glucose, lactate, oxygen, and the like, in certain individuals is vitally important to their health. For example, the monitoring of glucose is particularly important to individuals with diabetes. Diabetics may need to monitor glucose levels to determine when insulin is needed to reduce glucose levels in their bodies or when additional glucose is needed to raise the level of glucose in their bodies.

Devices have been developed for continuous or automatic monitoring of analytes, such as glucose, in bodily fluid such as in the blood stream or in interstitial fluid. Some of these analyte measuring devices are configured so that at least a portion of the devices are positioned below a skin surface of a user, e.g., in a blood vessel or in the subcutaneous tissue of a user.

The user's comfort and the range of activities that may be performed while a portion of the device is positioned below a skin surface are important considerations in designing extended-use sensors for continuous or automatic in vivo monitoring of the level of an analyte, such as glucose. There is a need for a small, comfortable device which may continuously monitor the level of an analyte, such as glucose, while still permitting the user to engage in normal activities. Continuous and/or automatic monitoring of the analyte may provide a warning to the user when the level of the analyte is at or near a threshold level. For example, if glucose is the analyte, then the monitoring device might be configured to warn the user of current or impending hyperglycemia or hypoglycemia. The user may then take appropriate actions.

One of the challenges associated with producing an effective and comfortable monitoring device is securing an element of the monitoring device to the skin. A monitoring device element may be attached to the skin with an adhesive. However, adhesives eventually lose their adhesive properties. Also, outer layers of the skin continually slough off. Eventually, the loss of adhesion and sloughing off of the skin serve to detach the monitoring device element from the skin and the monitoring device element falls off of the user.

When the monitoring device element falls off of the skin, a new monitoring device element may have to be attached to the skin and a new sensor may have to be inserted into the skin. Accordingly, if a monitoring device falls off too quickly, its life is limited and a user must insert another sensor, adding to the cost of the monitoring device. Also, the more frequent insertions of sensors may cause skin trauma.

One manner of increasing the attachment time is to provide a stronger adhesive. However, increasing the strength of the adhesive makes removal of the monitoring device element from the skin more difficult and painful. Also, simply increasing the adhesive strength may not overcome the problems associated with outer layers of skin sloughing off the body. Accordingly, the present disclosure is directed to providing a structure and method of attaching an element of a monitoring device to a user's skin that will result in a longer-lasting attachment.

SUMMARY

Provided are methods and structures for securing an element of a monitoring device to a person's skin. In one embodiment a first adhesive is used to secure the element to a person's skin during a first time period and a second adhesive is used to secure the element to the person's skin during a second time period. A sensor may be at least partially inserted into the user's skin during the first and the second time periods and the element may include a housing for the sensor.

BRIEF DESCRIPTION OF THE DRAWINGS

The above aspects and features of the present disclosure will be more apparent by describing certain embodiments of the present disclosure with reference to the accompanying drawings, in which:

FIG. 2 shows a schematic diagram of an embodiment of an analyte sensor according to the present disclosure; and FIGS. 3A-3B show a perspective view and a cross sectional view, respectively of another embodiment of an analyte sensor.

DETAILED DESCRIPTION

Figure 1:
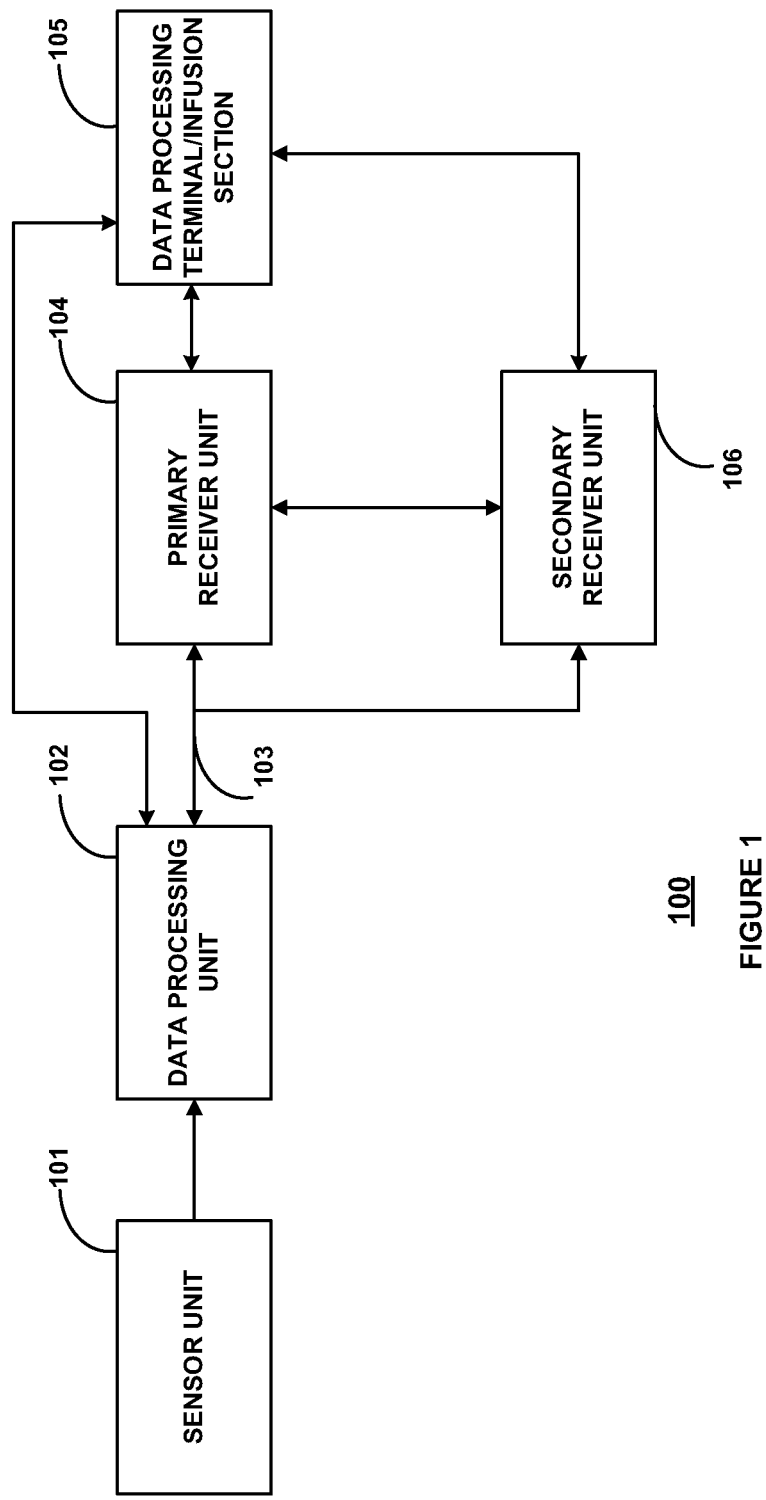
FIG. 1 is a block diagram of an exemplary embodiment of a data monitoring and management system according to the present disclosure.

Before the present disclosure is described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges as also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein may also be used in the practice or testing of the present disclosure, the preferred methods and materials are now described.

It must be noted that as used herein and in the appended claims, the singular forms "a", "an", and "the" include plural referents unless the context clearly dictates otherwise.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Embodiments include analyte monitoring devices and systems that include an analyte sensor—at least a portion of which is positionable beneath the skin of the user—for the in vivo detection, of an analyte, such as glucose, lactate, and the like, in a body fluid. Embodiments include wholly implantable analyte sensors and analyte sensors in which only a portion of the sensor is positioned under the skin and a portion of the sensor resides above the skin, e.g., for contact to a transmitter, receiver, transceiver, processor, etc. The sensor may be, for example, subcutaneously positionable in a user for the continuous or periodic monitoring of a level of an analyte in a user's interstitial fluid. For the purposes of this description, continuous monitoring and periodic monitoring will be used interchangeably, unless noted otherwise. The sensor response may be correlated and/or converted to analyte levels in blood or other fluids. In certain embodiments, an analyte sensor may be positioned in contact with interstitial fluid to detect the level of glucose, which detected glucose may be used to infer the glucose level in the user's bloodstream. Analyte sensors may be insertable into a vein, artery, or other portion of the body containing fluid. Embodiments of the analyte sensors of the subject disclosure may be configured for monitoring the level of the analyte over a time period which may range from minutes, hours, days, weeks, or longer.

Of interest are analyte sensors, such as glucose sensors, that are capable of in vivo detection of an analyte for about one hour or more, e.g., about a few hours or more, e.g., about a few days or more, e.g., about three days or more, e.g., about five days or more, e.g., about seven days or more, e.g., about several weeks or at least one month. Future analyte levels may be predicted based on information obtained, e.g., the current analyte level at time t0, the rate of change of the analyte, etc. Predictive alarms may notify the user of predicted analyte levels that may be of concern in advance of the user's analyte level reaching the future level. This provides the user an opportunity to take corrective action.

Embodiments described herein are applicable to attaching a device to a person's skin. As noted above, the exemplary embodiments described herein relate to attaching to a user's skin an element of an analyte monitoring system using an implantable sensor for the in vivo determination of a concentration of an analyte, such as glucose or lactate, in a fluid. However, although certain exemplary embodiments describe an analyte monitoring system, the disclosure is not limited to the particular system described herein. The structure and method of the present disclosure may be applied to other devices and particularly to devices adapted to be secured to a person's skin and also devices which include a sensor which is at least partially inserted into the person's skin.

FIG. 1 shows a data monitoring and management system such as, for example, an analyte (e.g., glucose) monitoring system 100 in accordance with certain embodiments. Embodiments of the subject disclosure are further described primarily with respect to glucose monitoring devices and systems, and methods of glucose detection, for convenience only and such description is in no way intended to limit the scope of the disclosure. It is to be understood that the analyte monitoring system may be configured to monitor a variety of analytes at the same time or at different times.

Analytes that may be monitored include, but are not limited to, acetyl choline, amylase, bilirubin, cholesterol, chorionic gonadotropin, creatine kinase (e.g., CK-MB), creatine, creatinine, DNA, fructosamine, glucose, glutamine, growth hormones, hormones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times.

The analyte monitoring system 100 includes a sensor unit 101, a data processing unit 102 connectable to the sensor unit 101, and a primary receiver unit 104 which is configured to communicate with the data processing unit 102 via a communication link 103. In certain embodiments, the primary receiver unit 104 may be further configured to transmit data to a data processing terminal 105 to evaluate or otherwise process or format data received by the primary receiver unit 104. The data processing terminal 105 may be configured to receive data directly from the data processing unit 102 via a communication link which may optionally be configured for bi-directional communication. Further, the data processing unit 102 may include a transmitter or a transceiver to transmit and/or receive data to and/or from the primary receiver unit 104 and/or the data processing terminal 105 and/or optionally the secondary receiver unit 106.

Also shown in FIG. 1 is an optional secondary receiver unit 106 which is operatively coupled to the communication link and configured to receive data transmitted from the data processing unit 102. The secondary receiver unit 106 may be configured to communicate with the primary receiver unit 104, as well as the data processing terminal 105. The secondary receiver unit 106 may be configured for bi-directional wireless communication with each of the primary receiver unit 104 and the data processing terminal 105. As discussed in further detail below, in certain embodiments the secondary receiver unit 106 may be a de-featured receiver as compared to the primary receiver, i.e., the secondary receiver may include a limited or minimal number of functions and features as compared with the primary receiver unit 104. As such, the secondary receiver unit 106 may include a smaller (in one or more, including all, dimensions), compact housing or embodied in a device such as a wrist watch, arm band, etc., for example. Alternatively, the secondary receiver unit 106 may be configured with the same or substantially similar functions and features as the primary receiver unit 104. The secondary receiver unit 106 may include a docking portion to be mated with a docking cradle unit for placement by, e.g., the bedside for night time monitoring, and/or a bi-directional communication device. A docking cradle may recharge a powers supply.

Only one sensor unit 101, data processing unit 102 and data processing terminal 105 are shown in the embodiment of the analyte monitoring system 100 illustrated in FIG. 1. However, it will be appreciated by one of ordinary skill in the art that the analyte monitoring system 100 may include more than one sensor unit 101 and/or more than one data processing unit 102, and/or more than one data processing terminal 105. Multiple sensors may be positioned in a user for analyte monitoring at the same or different times. In certain embodiments, analyte information obtained by a first positioned sensor may be employed as a comparison to analyte information obtained by a second sensor. This may be useful to confirm or validate analyte information obtained from one or both of the sensors. Such redundancy may be useful if analyte information is contemplated in critical therapy-related decisions. In certain embodiments, a first sensor may be used to calibrate a second sensor.

The analyte monitoring system 100 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 100. For example, unique IDs, communication channels, and the like, may be used.

In certain embodiments, the primary receiver unit 104 may include an analog interface section including an RF receiver and an antenna that is configured to communicate with the data processing unit 102 via the communication link 103, and a data processing section for processing the received data from the data processing unit 102 such as data decoding, error detection and correction, data clock generation, data bit recovery, etc., or any combination thereof.

In operation, the primary receiver unit 104 in certain embodiments is configured to synchronize with the data processing unit 102 to uniquely identify the data processing unit 102, based on, for example, an identification information of the data processing unit 102, and thereafter, to periodically receive signals transmitted from the data processing unit 102 associated with the monitored analyte levels detected by the sensor unit 101.

Referring again to FIG. 1, the data processing terminal 105 may include a personal computer, a portable computer such as a laptop or a handheld device (e.g., personal digital assistants (PDAs), telephone such as a cellular phone (e.g., a multimedia and Internet-enabled mobile phone such as an iPhone or similar phone), mp3 player, pager, and the like), drug delivery device, each of which may be configured for data communication with the receiver via a wired or a wireless connection. Additionally, the data processing terminal 105 may further be connected to a data network (not shown) for storing, retrieving, updating, and/or analyzing data corresponding to the detected analyte level of the user.

The data processing terminal 105 may include an infusion device such as an insulin infusion pump or the like, which may be configured to administer insulin to users, and which may be configured to communicate with the primary receiver unit 104 for receiving, among others, the measured analyte level. Alternatively, the primary receiver unit 104 may be configured to integrate an infusion device therein so that the primary receiver unit 104 is configured to administer insulin (or other appropriate drug) therapy to users, for example, for administering and modifying basal profiles, as well as for determining appropriate boluses for administration based on, among others, the detected analyte levels received from the data processing unit 102. An infusion device may be an external device or an internal device (wholly implantable in a user).

In certain embodiments, the data processing terminal 105, which may include an insulin pump, may be configured to receive the analyte signals from the data processing unit 102, and thus, incorporate the functions of the primary receiver unit 104 including data processing for managing the user's insulin therapy and analyte monitoring. In certain embodiments, the communication link 103 as well as one or more of the other communication interfaces shown in FIG. 1, may use one or more of: an RF communication protocol, an infrared communication protocol, a Bluetooth® enabled communication protocol, an 802.11x wireless communication protocol, or an equivalent wireless communication protocol which would allow secure, wireless communication of several units (for example, per HIPAA requirements), while avoiding potential data collision and interference.

FIG. 2 schematically shows an embodiment of an analyte sensor in accordance with the present disclosure. This sensor embodiment includes electrodes 401, 402 and 403 on a base 404. Electrodes (and/or other features) may be applied or otherwise processed using any suitable technology, e.g., chemical vapor deposition (CVD), physical vapor deposition, sputtering, reactive sputtering, printing, coating, ablating (e.g., laser ablation), painting, dip coating, etching, and the like. Materials include but are not limited to aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (e.g., doped polycrystalline silicon), silver, tantalum, tin, titanium, tungsten, uranium, vanadium, zinc, zirconium, mixtures thereof, and alloys, oxides, or metallic compounds of these elements.

The sensor may be wholly implantable in a user or may be configured so that only a portion is positioned within (internal) a user and another portion outside (external) a user. For example, the sensor 400 may include a portion positionable above a surface of the skin 410, and a portion positioned below the skin. In such embodiments, the external portion may include contacts (connected to respective electrodes of the second portion by traces) to connect to another device also external to the user such as a transmitter unit. While the embodiment of FIG. 2 shows three electrodes side-by-side on the same surface of base 404, other configurations are contemplated, e.g., fewer or greater electrodes, some or all electrodes on different surfaces of the base or present on another base, some or all electrodes stacked together, electrodes of differing materials and dimensions, etc.

FIG. 3A shows a perspective view of an embodiment of an electrochemical analyte sensor 500 having a first portion (which in this embodiment may be characterized as a major portion) positionable above a surface of the skin 510, and a second portion (which in this embodiment may be characterized as a minor portion) that includes an insertion tip 530 positionable below the skin, e.g., penetrating through the skin and into, e.g., the subcutaneous space 520, in contact with the user's biofluid such as interstitial fluid. Contact portions of a working electrode 501, a reference electrode 502, and a counter electrode 503 are positioned on the portion of the sensor 500 situated above the skin surface 510. Working electrode 501, a reference electrode 502, and a counter electrode 503 are shown at the second section and particularly at the insertion tip 530. Traces may be provided from the electrode at the tip to the contact, as shown in FIG. 3A. It is to be understood that greater or fewer electrodes may be provided on a sensor. For example, a sensor may include more than one working electrode and/or the counter and reference electrodes may be a single counter/reference electrode, etc.

FIG. 3B shows a cross sectional view of a portion of the sensor 500 of FIG. 3A. The electrodes 501, 502 and 503, of the sensor 500 as well as the substrate and the dielectric layers are provided in a layered configuration or construction. For example, as shown in FIG. 3B, in one aspect, the sensor 500, includes a substrate layer 504, and a first conducting layer 501 such as carbon, gold, etc., disposed on at least a portion of the substrate layer 504, and which may provide the working electrode. Also shown disposed on at least a portion of the first conducting layer 501 is a sensing layer 508.

A first insulation layer such as a first dielectric layer 505 is disposed or layered on at least a portion of the first conducting layer 501, and further, a second conducting layer 509 may be disposed or stacked on top of at least a portion of the first insulation layer (or dielectric layer) 505. As shown in FIG. 3B, the second conducting layer 509 may provide the reference electrode 502, and in one aspect, may include a layer of silver/silver chloride (Ag/AgCl), gold, etc.

A second insulation layer 506 such as a dielectric layer in one embodiment may be disposed or layered on at least a portion of the second conducting layer 509. Further, a third conducting layer 503 may provide the counter electrode 503. It may be disposed on at least a portion of the second insulation layer 506. Finally, a third insulation layer may be disposed or layered on at least a portion of the third conducting layer 503. In this manner, the sensor 500 may be layered such that at least a portion of each of the conducting layers is separated by a respective insulation layer (for example, a dielectric layer). The embodiment of FIGS. 3A and 3B show the layers having different lengths. Some or all of the layers may have the same or different lengths and/or widths.

In certain embodiments, some or all of the electrodes 501, 502, 503 may be provided on the same side of the substrate 504 in the layered construction as described above, or alternatively, may be provided in a co-planar manner such that two or more electrodes may be positioned on the same plane (e.g., side-by side (e.g., parallel) or angled relative to each other) on the substrate 504. For example, co-planar electrodes may include a suitable spacing there between and/or include dielectric material or insulation material disposed between the conducting layers/electrodes. Furthermore, in certain embodiments, one or more of the electrodes 501, 502, 503 may be disposed on opposing sides of the substrate 504. In such embodiments, contact pads may be on the same or different sides of the substrate. For example, an electrode may be on a first side and its respective contact may be on a second side, e.g., a trace connecting the electrode and the contact may traverse through the substrate.

The description herein is directed primarily to electrochemical sensors for convenience only and is in no way intended to limit the scope of the disclosure. Other sensors and sensor systems are contemplated. Such include, but are not limited to, optical sensors, calorimetric sensors, and sensors that detect hydrogen peroxide to infer glucose levels, etc. The sensor may be used as part of the sensor unit 101.

Figure 4:
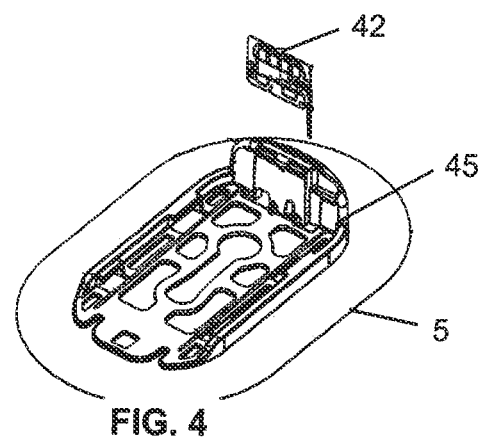
FIG. 4 is a perspective view of an exemplary embodiment of an on-skin sensor unit, according to the disclosure.
Figure 5:
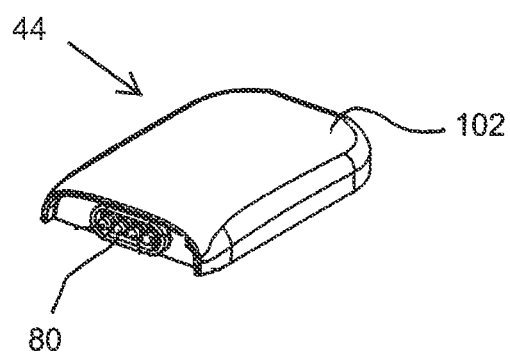
FIG. 5 is a top view of a cover of the on-skin sensor unit of FIG. 4.

At least some portions of the analyte monitoring system 100 may be attached on a user's skin. Exemplary embodiments of the present disclosure are described with reference to the sensor unit 101 and the data processing unit 102 being attached to a user's skin. However, other parts of the analyte monitoring system 100 may additionally or alternatively be attached to a user's skin FIGS. 4 and 5 show, respectively, an exemplary embodiment of a sensor unit 101 and a data processing unit 102 which can be coupled to a mount of the sensor unit 101. As shown in FIG. 4, there is a sensor mount/housing 45 which stays on a user's skin after the sensor is inserted into the user's skin. The sensor mount 45 holds the sensor 42 in place and holds the data processing unit/transmitter 102. An adhesive portion 5 is provided on the bottom of the sensor mount 45. As shown in FIG. 5, the data processing unit 102 of the exemplary embodiment is a wireless transmitter. The unit 102 includes tabs and guides which allow the unit 102 to slide into the mount 45 and hold the transmitter 102 in place. Additionally, the transmitter unit 102 comprises contact points 80 which connect the sensor 42 to the transmitter. Together, these units provide an on-skin unit 44.

The on-skin unit 44 may be formed in a shape that is comfortable to the user and which may permit concealment, for example, under a user's clothing. The thigh, leg, upper arm, shoulder, or abdomen are convenient parts of the user's body for placement of the on-skin sensor unit 44 to maintain concealment. However, the on-skin unit 44 may be positioned on other portions of the user's body. One embodiment of the on-skin sensor unit 44 has a generally rectangular shape to enhance concealment, as illustrated in FIGS. 4 and 5. However, other shapes and sizes, such as a thin oval shape, may be used.

The particular profile, as well as the height, width, length, weight, and volume of the on-skin unit 44 may vary and depends, at least in part, on the components and associated functions included in the on-skin sensor unit 44, as discussed below. For example, in some embodiments, the on-skin unit 44 may have a height of about 2 cm or less, 1.3 cm or less, or about 0.7 cm or less. In some embodiments, the on-skin unit 44 may have a weight of about 90 grams or less, e.g., about 45 grams or less, e.g., about 25 grams or less. In some embodiments, the on-skin unit 44 has a volume of about 15 $cm^3$ or less.

The sensor mount 45, illustrated in FIGS. 4 and 5, may be formed using a variety of materials, including, for example, plastic and polymeric materials, particularly rigid thermoplastics and engineering thermoplastics. Suitable materials include, for example, polyvinyl chloride, polyethylene, polypropylene, polystyrene, ABS polymers, and copolymers thereof. The mount 45 may be formed using a variety of techniques including, for example, injection molding, compression molding, casting, and other molding methods. Hollow or recessed regions may be formed in the sensor mount 45 of the on-skin unit 44. The electronic components of the on-skin unit 44, described below, and/or other items, such as a battery or a speaker for an audible alarm, may be placed in the hollow or recessed areas.

Conductive contacts 80 may be formed on the exterior of the transmitter 102 which connect to the sensor 42.

Figure 6:
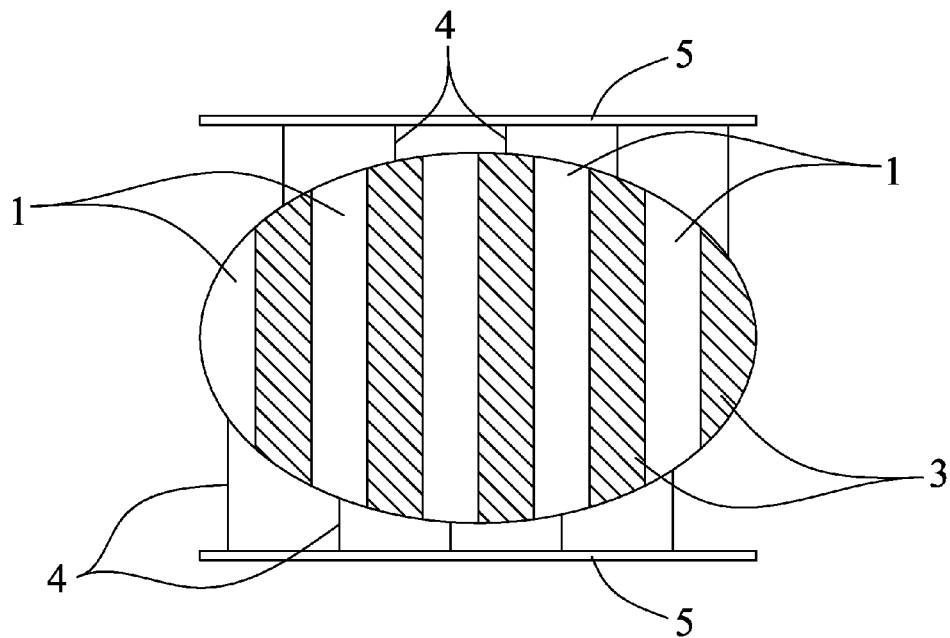
FIG. 6 is bottom view of an on-skin sensor unit with adhesives according to an exemplary embodiment of the present disclosure.
Figure 7:
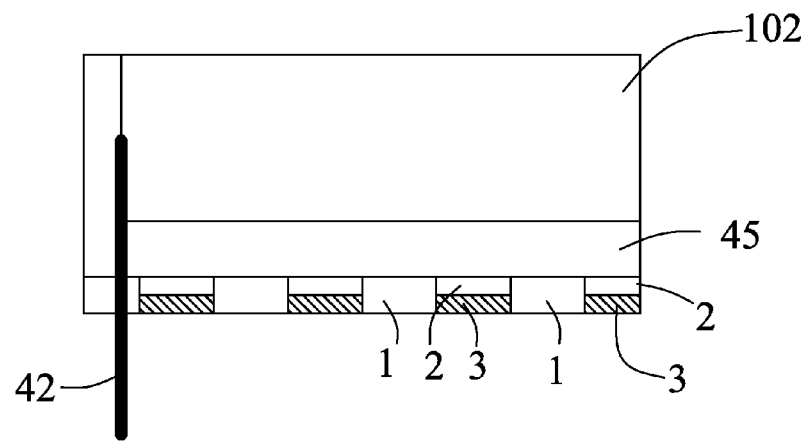
FIG. 7 is a side view of the on-skin sensor unit of FIG. 6.

FIGS. 6 and 7 show exemplary embodiments of the sensor unit with a plurality of discrete adhesive portions on a surface, e.g., a bottom of the sensor mount 45 for securing the on-skin unit 44 to a user's skin. FIG. 6 is a bottom view of the on-skin unit 44 and FIG. 7 is a cross-sectional side view of the on-skin unit 44. The sizes of the adhesive portions may be exaggerated in the drawings for purposes of explanation.

As shown in FIGS. 6 and 7, a first adhesive 1 and a second adhesive 2 are provided on a bottom of the sensor mount 45. The first adhesive 1 is used to secure the on-skin unit 44 to the user's skin during a first time period and the second adhesive 2 is used to secure the on-skin unit 44 to the user's skin during a second time period. During the second time period, the first adhesive may remain on the on-skin unit 44 and work with the second adhesive or may be removed to expose the base of the sensor mount 45.

As shown in FIGS. 6 and 7, removable coverings 3 cover the second adhesive 2 and optional protrusions 4 are attached to the removable covering 3. The protrusions are used to help remove the coverings 3 and expose a surface of the second adhesive 2. Since the protrusions 4 are attached to the coverings 3, pulling on the protrusions 4 removes the coverings 3. The protrusions 4 may be thin strings. However, the protrusions are not limited to thin strings, and other materials may be used to form the protrusions 4. As shown in FIG. 6, a tab 5 may be attached to the protrusions 4. The tab 5 allows for all of the coverings 3 to be removed at once by pulling on the tab 5, rather than the individual protrusions 4. The unit 44 remains on the user's skin during the time that the second adhesive 2 is uncovered and used for attachment.

As noted above, after the second adhesive is exposed for securing the on-skin unit 44, the first adhesive 1 may also be removed. Accordingly, for example as shown in FIG. 6, protrusions 4 (or other contacts) if provided may also be attached to the first adhesive 1. These protrusions 4 may also be attached to a tab 5 for easier removal.

In FIGS. 6 and 7, the first and second adhesives are patterned in the form of alternating stripes. This configuration allows for a generally uniform distribution of the first and second adhesive 1, 2. This configuration also allows for the coverings 3 of the second adhesive to be removed without disturbing the first adhesive 1. Also, it allows the first adhesive 1 to be removed without disturbing the second adhesive. The adhesives may be arranged in other configurations as well. For example, other configurations include, but are not limited to, dots, intersecting stripes, etc.

Figure 8:
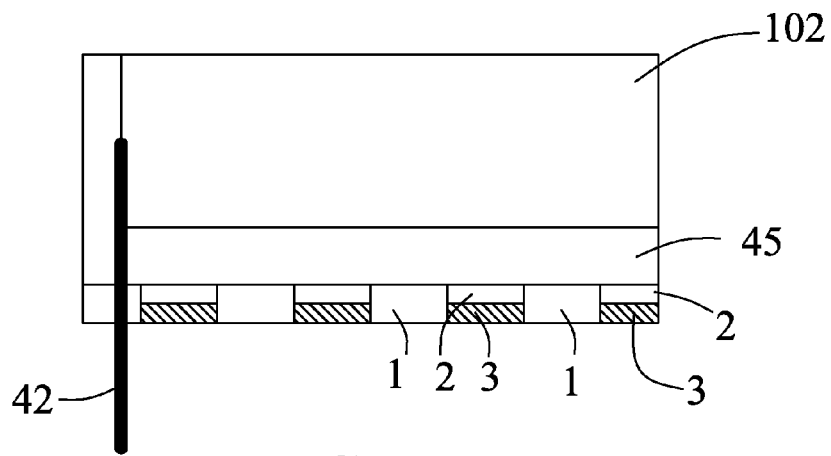
FIG. 8 is a side view of the on-skin sensor unit of FIG. 6 attached to a user's skin during a first time period.
Figure 9:
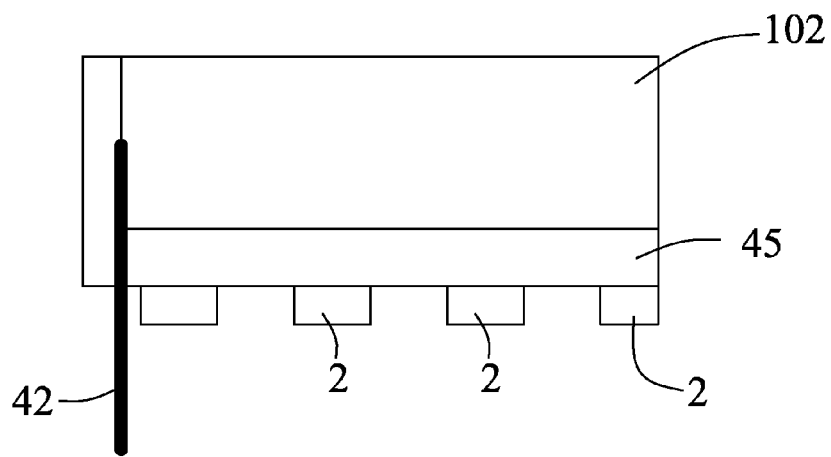
FIG. 9 is a side view of the on-skin sensor unit of FIG. 6 attached to a user's skin during a second time period.

FIGS. 8 and 9 illustrate a method of using of the adhesive structure of FIGS. 6 and 7 to attach the on-skin unit 44 to a user's skin according to certain embodiments. As shown in FIG. 8, initially the first adhesive is exposed and the second adhesive is covered by coverings 3. The first adhesive thus secures the sensor to the skin S (FIGS. 10-13B) of a user for a first time period. This time period may be any suitable period, e.g., approximately three days or longer, e.g., approximately five days or longer, e.g., approximately seven days or longer, although the duration is not particularly limited and may be substantially longer or shorter than about three days.

At the end of the first time period, the coverings 3 are removed. This may be done by pulling on the individual protrusions 4 or, if included, by pulling on a tab 5 attached to each of the protrusions 4. The coverings 3 may also be removed in other manners which do not require the protrusions 4 or tab 5. When the coverings 3 are removed, the second adhesive 2 is exposed to contact the skin, and may be pressed on the skin S to maintain contact if necessary. During the removal of the covering 3 and the pressing of the second adhesive, the sensor 42 remains at least partially inserted into the user's skin S, i.e., remains in analyte monitoring position. While the coverings 3 are being removed, the first adhesive may continue to secure the sensor mount 45 to the user's skin.

As shown in FIG. 9, after the coverings 3 are removed, the on-skin unit 44 may be pressed against the skin so that the fresh second adhesive 2 attaches to the user's skin. The second adhesive 2 then secures the sensor unit to the user's skin for a second time period. Again, this second time period is not particularly limited, but may be analogous to that described above of the first time period. The user may remove the sensor at the end of a specified second time period, or the on-skin unit 44 may simply remain on the user's skin until it falls off. In certain embodiments, third, fourth, fifth, ... adhesives may be included and the process may be repeated as appropriate to extend the adhesion time to the skin.

As shown in FIG. 9, after the second adhesive 2 is exposed and helps secure the on-skin unit 44 to the skin S, the first adhesive may be removed by the protrusions 4 and tab 5 described above. Alternatively, the first adhesive 1 may simply remain on the on-skin unit 44 during the second time period. If the first adhesive 1 remains on the sensor mount 45, it may work in conjunction with the second adhesive 2 during the second time period.

Accordingly, according to the exemplary embodiment of FIGS. 8 and 9, the adhesive used to secure the on-skin unit 44 may be refreshed or renewed without removing the sensor 42 from a user's skin. Because the adhesive is refreshed, the on-skin unit 44 may remain on the user's skin for a longer period of time without using an unnecessarily strong adhesive. This may increase the life of the on-skin unit 44 and the sensor 42 and may avoid unnecessary trauma to the skin by excessive insertion of the sensor 42. Also, it may avoid the inconvenience for the user of having to frequently replace the sensor 42 and on-skin unit 44. The use of the multiple adhesives as described in the exemplary embodiment may also decrease the chances of an adverse reaction to the adhesives, since the adhesive site may be changed between the use of the first and second adhesives.

The first adhesive 1 and the second adhesive 2 may be the same adhesive material or may be different adhesives, same or different shape, size, etc. Also, they may have the same or different strengths. For example, the first adhesive 1 may be made stronger to ensure that the sensor mount 45 does not fall off before the user exposes the second adhesive 2. The second adhesive may be made less strong so that the user may comfortably remove the sensor unit from the skin at the end of the second time period.

Figure 10:
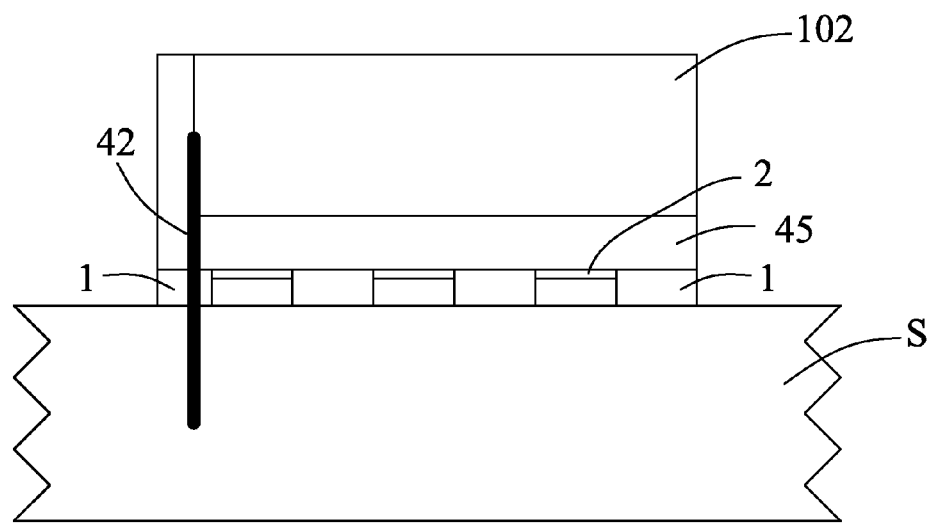
FIG. 10 is a side view of an on-skin sensor unit with adhesives according to another exemplary embodiment of the present disclosure and attached to a user's skin during a first time period.
Figure 11:
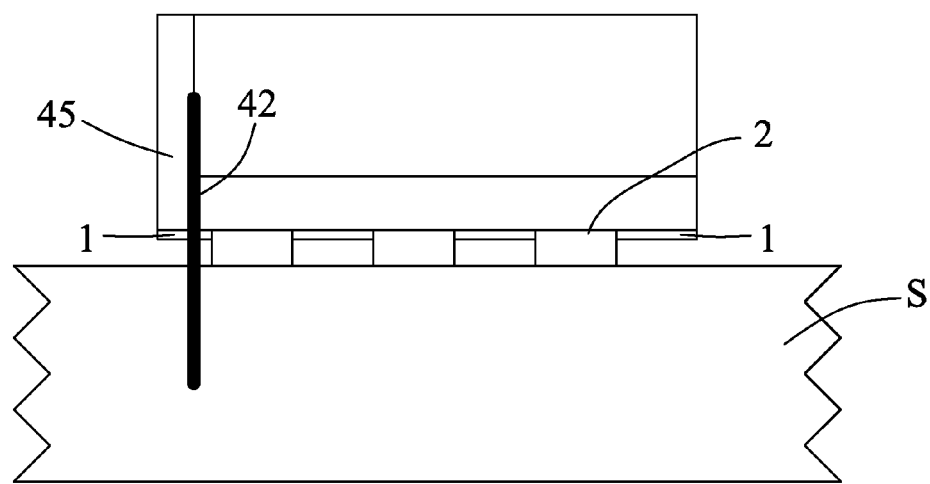
FIG. 11 is a side view of the on-skin sensor unit with adhesives of FIG. 10 and attached to a user's skin during a second time period.

FIGS. 10 and 11 illustrate another exemplary embodiment of an on-skin unit 44 attachment method and structure. FIG. 10 is a side view of the on-skin unit 44 in a first configuration during a first time period. Like the previous exemplary embodiment, there is both a first adhesive 1 and a second adhesive 2. The first adhesive 1 secures the on-skin unit 44 to the user's skin S during the first period and a fresh second adhesive 2 is used during a second time period. As shown in FIG. 10, during the first time period, the first adhesive 1 is at a lower position so that it may contact the user's skin S and secure the sensor mount 45. As shown in FIG. 11, after the first period, the second adhesive 2 is moved to a position of contacting the skin and securing the sensor unit. This may occur by switching the positions of the first and second adhesives. Alternatively, the first adhesive 1 may be removed. In any event, there may be a covering over the second adhesive 2 which is removed before it is contacted with the skin S.

The positions of the first and second adhesives may be changed in a variety of different ways. One possible manner is to use a cam to press the areas of the first adhesives down during the first time period and the second adhesives down during a second time period. The areas of the sensor mount 45 may be biased in the upward direction. Accordingly, when the cam is in a position of pressing areas corresponding to the first or second adhesive downwardly, the pressed areas move downward. When the first or second adhesive is not pressed downward by a portion of the cam, the adhesive returns up. Alternatively, the areas on which the first and second adhesives are mounted may simply be mechanically drivable up and down, but the turning of a gear or the like. Mechanical methods may include a simple press-down on either side of the device with a 2 pronged fork or a twisting action to rotate an axle between a wheel/cylinder at either end of the device, resembling the turn of a key. The motion may also be accomplished in an electrical manner which provides similar mechanical movement powered automatically by an attached motor. Other mechanical and electrical methods for moving the first and second adhesives are also possible.

Figure 12:
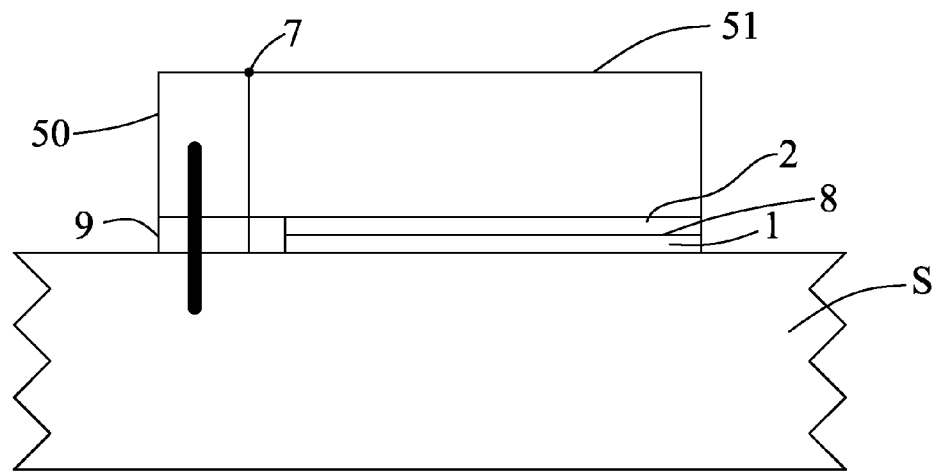
FIG. 12 is a side view of an on-skin sensor unit with adhesives according to another exemplary embodiment of the present disclosure and attached to a user's skin during a first time period.
Figure 13A:
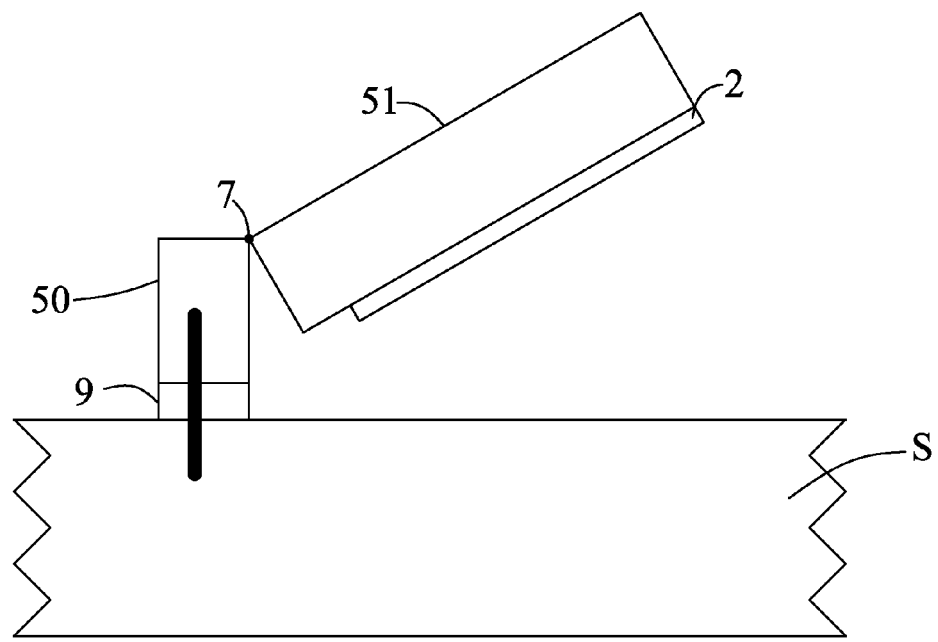
FIGS. 13A and 13B are side and perspective views, respectively, of the on-skin sensor unit with adhesives shown in FIG. 12 with a portion of the control unit lifted from the user's skin.
Figure 13B:
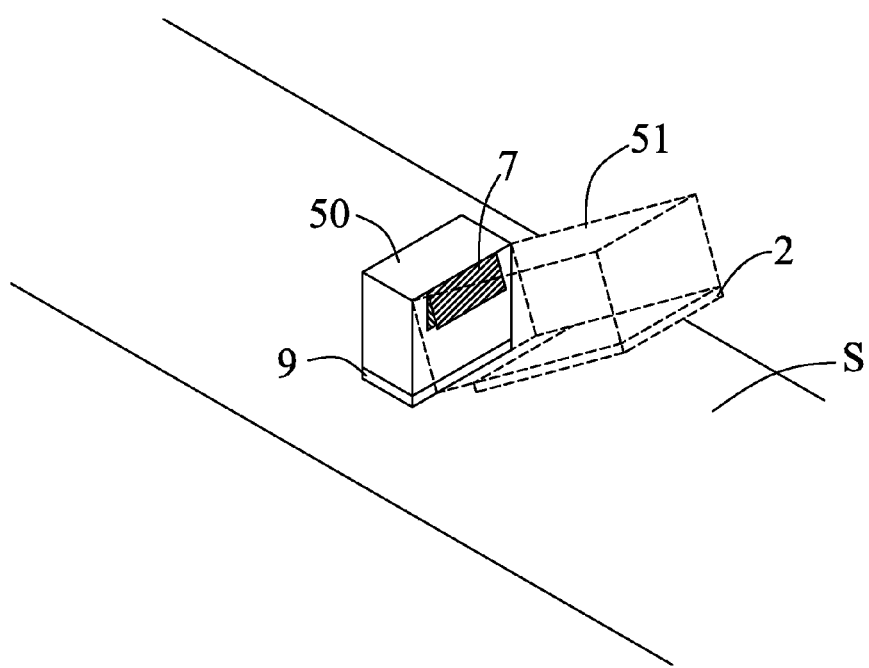

FIGS. 12, 13A and 13B show another exemplary embodiment of the disclosure. According to this exemplary embodiment, a first adhesive 1 and a second adhesive 2 are layered on the bottom of the on-skin unit 44. During the first time period, the sensor 42 is at least partially inserted into the skin S and the sensor mount 45 of the sensor unit is secured to the skin S by the first adhesive 1. In this exemplary embodiment, the on-skin unit 44 includes a hinge 7. The hinge allows a hinged portion 51 of the on-skin unit 44 to be hingedly rotated around a sensor portion 50 of the on-skin unit 44. As shown in FIG. 13A, after the first time period (e.g., three days) has passed, hinge portion 51 may be rotated around the hinge 7. The sensor portion 50, which includes the sensor 42 remains in the same location as the hinged portion 51 is lifted. Thus, the sensor 42 may remain in the skin and functioning during this time. After the hinged portion 51 is lifted, the first adhesive 1 is removed and the second adhesive 2 is exposed. In FIG. 13B, the hinged portion 51 is drawn in shadow to illustrate the hinge 7 in further detail. As shown in FIG. 13B, in this exemplary embodiment of the hinge 7, one leaf is attached to the sensor portion 50 and another leaf is attached to the hinged portion 51 and the leaves are connected at a corner portion of the sensor and hinge portions 50, 51 to allow the hinged portion 51 to rotate away from the user's skin relative to the sensor portion 50. The disclosure is not limited to the hinge shown in FIG. 13B and other types of hinges and manners of hinging the hinged portion 51 to the sensor portion 50 may also be used.

In this exemplary embodiment, a partition 8 is located between the first adhesive 1 and the second adhesive 2. The partition 8 separates the first 1 and second adhesive 2. The partition 8 also serves as a covering for the second adhesive 2. Removing the partition 8 peels off the first layer of adhesive 1 and exposes the second layer of adhesive 2. The hinged portion 51 may then be swiveled back around the hinge 7 so that the second adhesive 2 contacts the skin S and secures the on-skin unit 44. In this manner, the adhesive securing the on-skin unit 44 is refreshed without disturbing the sensor 42.

Additionally, as shown in FIGS. 12, 13A and 13B, there may be an area with no adhesive at an edge of the hinged portion. This area of no adhesive helps to allow the hinged portion 51 to swivel away from the skin S.

The on-skin unit 44 may be hinged and swiveled in various directions. For example, instead of or in addition to being lifted vertically away from the skin, the hinged portion 51 may be rotated around the sensor 42. Rotating the location of the hinged portion 51 allows the second adhesive 2 to be attached to a fresh site, at least partially different than the area of skin to which the first adhesive 1 was attached. This helps to alleviate some of the problems associated with the sloughing off of skin and may also prevent problems associated with an adverse skin reaction to the adhesive by lessening the time that the adhesive is attached to a particular area of the skin.

Also, a sensor area adhesive 9 may be provided around the sensor 42 at the sensor portion 50. The insertion of the sensor 42 itself provides at least some attachment to the skin. Also, the sensor 42 may be provided with a barb or other structure to increase its attachment in the skin S. The sensor area adhesive 9 provides an additional degree of attachment of the sensor portion 50 to the skin so that when the hinged portion 51 is being swiveled, the sensor does not fall out of the user's skin. The sensor area adhesive 9 may be stronger than the first and second adhesives. Particularly, the sensor area adhesive 9 may be designed to effectively last throughout the first and second time periods, or at least through the first time period and the swiveling of the hinged part 51.

The first and second adhesives 1, 2 may be either solid or formed in a pattern such as stripes or concentric circles. Also, the first and second adhesives may be the same adhesive or different adhesives. For example, the first adhesive 1 may be made stronger than the second adhesive 2 to ensure that it lasts until the user exposes and uses the second adhesive 2. Alternatively, the first adhesive 1 may be made less strong so that the user may swivel the on-skin unit 44 away from the skin S.

Figure 14:
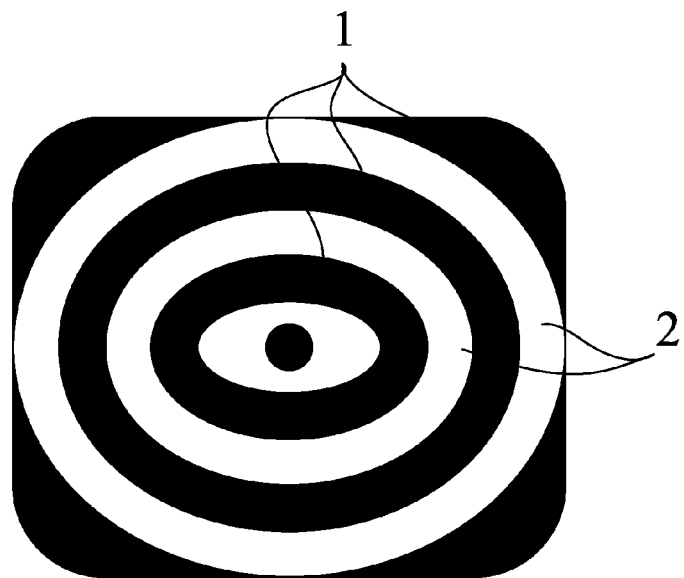
FIG. 14 is a bottom view of an on-skin sensor unit with adhesives according to an exemplary embodiment of the present disclosure.

According to another exemplary embodiment, shown in FIG. 14, first and second adhesives 1, 2 are patterned on the bottom of the on-skin unit 44 and are used at the same time to secure the on-skin unit 44 to the user's skin. In this exemplary embodiment, the first and second adhesives have different strengths and/or other properties. For example, the first adhesive 1 may be stronger than the second adhesive 2. The strong first adhesive would ensure that the sensor mount 45 is strongly bonded to the user's skin while the second adhesive 2 would also provide some assistance in securing the on-skin unit 44, but would also balance comfort in removal. Accordingly, this exemplary embodiment balances the characteristics of the first adhesive 1 and the second adhesive 2.

The first and second adhesives 1, 2 may be arranged in a striped manner. Another possibility is to arrange the first and second adhesives 1, 2 in a pattern of concentric circles, as shown in FIG. 14. These two patterns would allow a relatively good mixing and spacing of the two different adhesives. However, the disclosure is not limited to these two patterns.

Figure 15:
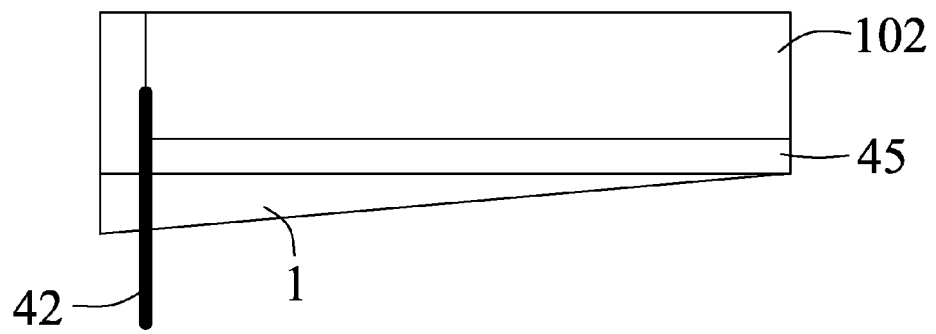
FIG. 15 is a side view of an on-skin sensor unit with an adhesive according to an exemplary embodiment of the present disclosure.

FIG. 15 illustrates another exemplary embodiment. In this exemplary embodiment only a first adhesive 1 is required, but the thickness of the adhesive is varied over the surface of the on-skin unit 44. For example, the adhesive is layered thickly at the left side of the on-skin unit 44 and is increasingly thinly towards the right side. Thickness is a factor in skin adhesion and the duration which the adhesive may secure the sensor control device to a user's skin. Therefore, varying the thickness of the adhesive over the on-skin unit 44 allows for balancing of the different characteristics provided by different thicknesses.

Varying thicknesses of adhesive could also be used in the exemplary embodiments with more than one adhesive. Also, the different adhesive patterns disclose, including striped and concentric circles, could be used in any of the exemplary embodiments.

Figure 16:
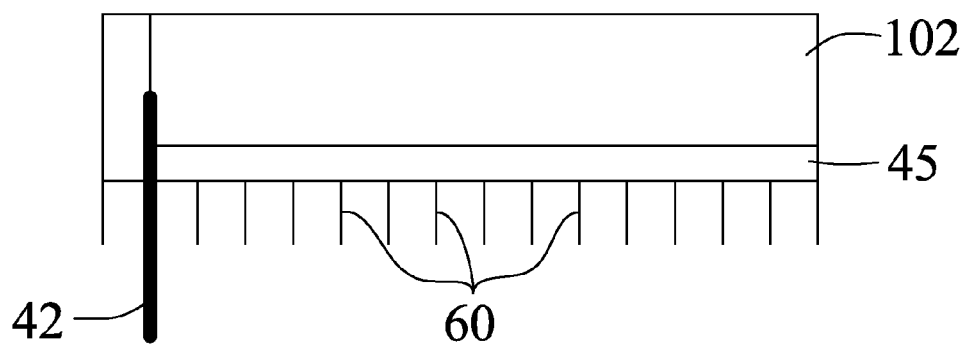
FIG. 16 is a side view of an on-skin sensor unit with a plurality of microneedles according to an exemplary embodiment of the present disclosure.

In another exemplary embodiment, shown in FIG. 16, microneedles are used to help attach an on-skin unit 44 to the user. As shown in FIG. 16, the microneedles 60 of the exemplary embodiment protrude from a bottom surface of the sensor mount 45. The microneedles help attach the on-skin unit 44 to the user by being at least partially inserted into the user's skin. The microneedles then catch or grab the user's skin, holding the on-skin unit 44 in place. In FIG. 16 the microneedles 60 are shown alone, without any adhesive.

However, the microneedles 60 may also be used in combination with an adhesive. The microneedles 60 may protrude at an angle in the range of 45° to 90° with respect to the sensor mount 45 in accordance with the desire for balancing the strength of the attachment to the user's skin and the ease of insertion and removal of the microneedles 60 from the user's skin.

The on-skin unit 44 described in the above exemplary embodiments is not particularly limited. In the exemplary embodiments, the on-skin unit 44 comprises a sensor 42 and sensor mount 45 to which a transmitter 102 is coupled. However, the on-skin unit adhered to the user's skin may include elements other than those shown in the exemplary embodiments. For example, the on-skin unit 44 may comprise only a sensor. Alternatively, the on-skin unit 44 could include a variety of other components which are part of an analyte monitoring system or other system.

Also, the exemplary embodiment of the disclosure has been described with respect to an on-skin unit 44 for use with an analyte monitoring system 100. However, the attachment structure and methods described above may be applied to any of a variety of objects and devices which need to be secured, particularly those objects which need to be secured to someone's skin and which include a sensor or other device which should remain in the same place throughout an attachment. For example, the securement structures and methods described above could be applied to additional or alternative portions of the analyte monitoring system 100. That is, in another embodiment all of the elements of the sensor control element 101 of the analyte monitoring system 100 would not necessarily have to be located on the user's skin. The present disclosure could be applied to an inserted sensor without a transmitter 102. Furthermore, the attachment methods and structures described above could be applied to devices other than elements of an analyte monitoring system such as an on-body insulin patch or infusion set/cannula of a pump system, or the drug delivery patch of another type of drug delivery system, for example, for pain medication, birth control, depression, etc. Particularly, devices for attachment to a person's skin. These devices may include at least a portion of an element, such as a sensor, inserted into a person's skin.

A monitoring device element in one embodiment includes a mount, a first adhesive on a surface of the housing and adapted to secure the mount to the skin for a first time period, and a second adhesive on the surface of the housing and adapted to secure the mount to the skin for a second time period.

The first adhesive and the second adhesive may be arranged in an alternating pattern, where the alternating pattern may include alternating stripes.

The monitoring device element may include at least one protrusion attached to the first adhesive, where the first adhesive is removable from the mount by pulling on the at least one protrusion.

In another aspect, the monitoring device element may include a removable covering over the second adhesive, where when the removable covering is removed, the second adhesive is exposed.

The monitoring device element may include at least one protrusion attached to the removable covering so that the removable covering is removed by pulling on a second protrusion.

In another aspect, at least the second adhesive may be movable between a raised position and a lowered position, where the second adhesive may be at the raised position during the first time period and at the lower position during the second time period.

The monitoring device element in still another aspect includes a glucose sensor mounted on the mount, at least one of a transmitter, receiver or transceiver attached to the mount and coupled to the sensor.

A method in another aspect includes inserting a sensor at least partially into the skin, the sensor being supported by a sensor housing, securing the sensor housing to the skin with a first adhesive during a first time period, and securing the sensor housing to the skin with a second adhesive during a second time period, the second time period being after the first time period, where the sensor remains at least partially inserted into the skin between the first time period and the second time period.

The method may include removing a covering to expose the second adhesive before securing the sensor housing to the skin with the second adhesive.

In another aspect, the method may include removing the first adhesive after the first time period.

Also, the method may include, between said first time period and said second time period, lifting the sensor housing so that the first adhesive no longer contacts the skin, removing the first adhesive to expose the second adhesive, and lowering the sensor housing so that the second adhesive contacts the skin. Additionally, the method may include swiveling the sensor housing before lowering the sensor housing so that the second adhesive contacts the skin at a different location than the first adhesive.

A monitoring device element in accordance with another aspect of the present disclosure includes a sensor at least partially inserted into skin, a sensor housing supporting the sensor, the sensor housing comprising a sensor area and a hinged area, a hinge hingedly connecting the sensor area and the hinged area, and a first adhesive and a second adhesive layered on a bottom surface of the hinged area, where the first adhesive is adapted to secure the sensor housing to the skin during a first time period and is removable, and where removing the first adhesive exposes the second adhesive, the second adhesive being adapted to secure the sensor housing to the skin during a second time period.

The monitoring device element may include a partition between the first adhesive and the second adhesive, where the first adhesive is removed and the second adhesive is exposed by removing the partition.

In one aspect, the monitoring device element may include a third adhesive at a bottom surface of the sensor area, the third adhesive securing the sensor area to the skin.

The hinge in one aspect may allow the hinged area to rotate away from the skin.

In another aspect, the hinge may allow the hinged area to swivel around the sensor area in a plane substantially parallel to the skin.

A monitoring device element in accordance with another aspect may include a sensor adapted to be at least partially inserted into skin, a housing which houses the sensor, a first adhesive and a second adhesive provided on a bottom of the sensor housing and being adapted to secure the sensor housing to a user's skin, where the first adhesive is stronger than the second adhesive, and further, where the first adhesive and the second adhesive are formed in a pattern so that the first adhesive contacts some areas of the skin and the second adhesive contacts other areas of the skin.

The pattern may include concentric circles, or alternating stripes.

A monitoring device element in still another aspect may include a sensor adapted to be at least partially inserted into skin, a housing which houses the sensor, an adhesive provided on a bottom of the sensor housing and being adapted to secure the sensor housing to a user's skin, where a thickness of the adhesive varies.

A device element in still yet another aspect includes a sensor mount supporting a sensor, a plurality of microneedles protruding from the sensor mount and being adapted for insertion into a user's skin.

Accordingly, while non-limiting exemplary embodiments of the disclosure have been described and illustrated above, it should be understood that these are examples of the disclosure and are not to be considered as limiting. It will be understood by those of ordinary skill in the art that additions, omissions, substitutions, and other modifications may be made without departing from the spirit or scope of the present disclosure.

What is claimed is:

1. A monitoring device element, comprising:
    a mount;
    a first adhesive on a surface of the mount and adapted to secure the mount to a skin surface for a first time period;
    a second adhesive on the surface of the mount and adapted to secure the mount to the skin surface for a second time period; and
    a removable covering over the second adhesive;
        wherein when the removable covering is removed, the second adhesive is exposed; and further
        wherein the mount remains secured to the skin surface during the removal of the removable covering.

2. The monitoring device element of claim 1, wherein the first adhesive and the second adhesive are arranged in an alternating pattern.

3. The monitoring device element of claim 2, wherein the alternating pattern comprises alternating stripes.

4. The monitoring device element of claim 1, comprising:
    at least one protrusion attached to the first adhesive;
        wherein the first adhesive is removable from the mount by pulling on the at least one protrusion.

5. The monitoring device element of claim 1, further comprising at least one protrusion attached to the removable covering so that the removable covering is removed by pulling on the at least one protrusion.

6. The monitoring device element of claim 1, wherein the second adhesive is movable between a raised position and a lowered position.

7. The monitoring device element of claim 6, wherein the second adhesive is at the raised position during the first time period and at the lowered position during the second time period.

8. The monitoring device element of claim 1, further comprising:
    a glucose sensor; and
    communication unit attached to the mount and coupled to the sensor.

9. A method of attaching the monitoring device element of claim 1, comprising:
    securing the mount to the skin surface with the first adhesive during the first time period, wherein the first adhesive is positioned on the surface of the mount and adapted to secure the mount to the skin surface for the first time period; and
    securing the mount to the skin surface with the second adhesive during the second time period, the second time period being after the first time period, wherein the second adhesive is positioned on the surface of the mount and adapted to secure the mount to the skin surface for the second time period; and
    removing the removable covering positioned over the second adhesive to expose the second adhesive before securing the mount to the skin surface with the second adhesive;
        wherein the mount remains secured to the skin surface during the removal of the removable covering.

10. The method of claim 9, further including inserting a sensor at least partially under the skin surface, the sensor being supported by a sensor housing including the mount.

* * * * *

UNITED STATES PATENT AND TRADEMARK OFFICE
CERTIFICATE OF CORRECTION

| | | |
|---|---|---|
| PATENT NO. | : 8,641,618 B2 | Page 1 of 1 |
| APPLICATION NO. | : 12/147462 | |
| DATED | : February 4, 2014 | |
| INVENTOR(S) | : R. Curtis Jennewine et al. | |

It is certified that error appears in the above-identified patent and that said Letters Patent is hereby corrected as shown below:

Claims:
Col. 16, Claim 8, line 4, change "communication unit" to --a communication unit--

Signed and Sealed this
Eighth Day of April, 2014

Michelle K. Lee
*Deputy Director of the United States Patent and Trademark Office*